US00RE39061E

(19) United States
(12) Reissued Patent
Anastassaki et al.

(10) Patent Number: US RE39,061 E
(45) Date of Reissued Patent: Apr. 11, 2006

(54) PHARMACEUTICAL FORMULATIONS COMPRISING LABDANES FOR THE TREATMENT OF TUMORS OR LEUKEMIAS

(75) Inventors: Thalia Anastassaki, Maroussi (GR); Demetra Angelopoulou, Ekali (GR); Demetrios Kokkinopoulos, Kifissia (GR); Constantinos Dimas, Pireas (GR); Constantinos Demetzos, Keratisini (GR)

(73) Assignee: Medexis S.A., Kryoneri (GR)

(21) Appl. No.: 10/965,712

(22) Filed: Oct. 14, 2004

Related U.S. Patent Documents

Reissue of:
(64) Patent No.: 6,652,877
Issued: Nov. 25, 2003
Appl. No.: 09/708,289
Filed: Nov. 8, 2000

(30) Foreign Application Priority Data

Nov. 8, 1999 (GR) ..... 990100387

(51) Int. Cl.
*A61K 9/127* (2006.01)
*A61K 9/133* (2006.01)

(52) U.S. Cl. ..... 424/450; 424/725; 514/451; 514/732

(58) Field of Classification Search ..... 424/450, 424/725; 514/25, 451, 724, 732
See application file for complete search history.

(56) References Cited

U.S. PATENT DOCUMENTS 4,529,561 A * 7/1985 Hunt
5,156,766 A * 10/1992 Behan
5,510,113 A * 4/1996 Bonte

OTHER PUBLICATIONS

Ahmed, A. "A diterpene xyloside from *Conza steudellii*." Phytochemistry, 1991, 30, 611–12.

Alcarez, M.J.; Garcia–Ochoa, S.; Jimenez, M.J.; Valverde, S.; Villar, A. "A derivative of ent–13–epi–manoyl oxidase isolated from *Sideritis javalambrensis*." Phytochemistry, 1989, 28, 1267–8.

Alcaraz, M.J.; Jimenez, M.J.; Valverde, S.; Sanz, J.; Rabanal, R.M. "Anti–inflammatory compounds from *Sideritis javalambrensis* N–hexane extract." J. Nat. Prod. 1989, 52, 1088–1091.

Atanasova–Shopova, S.; Rusinov, K. Izv. Inst. Fiziol. Bulg. Akad. Nauk., 1970, 13, 89. "Experimental studies on certain effects of the essential oil of Salvia Sclarea L. on the central nervous system." Chem. Abstr. 74, 123553 m, 1971, 89–95.

Ayafor, FJ; Tchuendem, MHK; Nyasse, B; Tillequin, F; Anke, H. "Novel bioactive diterpenoids from *Aframomum aulacocarpos*." J. Natural Products, 1994, 57(7), 917–23.

Barua, S.K.; Saha, S.K.; Patra, A.; Mitra, A.K. "The structure and stereochemistry of phlogantholide–A, a diterpene from *Phlogacanthus thyrsiflorus*." Phytochemistry, 1985, 24, 2037–39.

Bernardirelli, G.; Vial, C.; Starkemann, S.; Naf, F. "Structure and absolute configuration of (–)–sclareol–8–acetate." Acta Cryst., 1988, 44C, 715–7.

Bhat, S.V.; Balwa, B.S.; Dornauer, H.; de Souza, N.J.; Fehlhaber, H.W. "Structures and stereochemistry of new labdane diterpenoids from *Coleus forskohlii briq*." Tetrahedron Lett., 1977, 1669–72.

Bohlmann, F.; Suwita, A.; King, R.M.; Robinson, H. "New ent labdane derivatives from *Austroeupatorium–chaparense*." Phytochemistry, 1980, 19, 111–4 (in German with English Abstract).

Bohlmann, F.; Banerjee, S.; Jakupovic, J.; Grenz, M.; Mirsa, L.N.; Schmeda–Hirschmann, G.; King, R.M. "Clerodane and labdane diterpenoids from *Baccharis* species." Phytochemistry, 1985, 24, 511–5.

Bohlmann, F.; Hartono, L.; Zdero, C.; Jakupovic, J. "Constituents of the genus *Oxylobus*." Phytochemistry, 1985, 24, 1111–2.

Brodsky, A; Davio, C; Shayo, C; Lemos Legnazzi, B; Barbosa, M. "Forskolin induces U937 cell line differentiation as a result of a sustained cAMP elevation." Eur. J. Pharmacol., 1998, 350(1), 121–7.

Calabuig, M.T.; Cortes, M.; Francisco, C.G.; Hernadez, R.; Suarez, E. "Labdane diterpenes from *Cistus symphytifolius*." Phytochemistry, 1981, 20, 2255–8.

Cambie, R.C.; Jablin, K.N.; Preston, A.F. "Chemistry of the podocarpaceae. XLIII. Utilization of 8α,13–epoxylabd–14–ene and related compounds for the preparation of ambergris–type compounds." Aust. J. Chem. 1972, 25, 1767–78.

Caputo, R.; Mangoni, L.; Monaco, P. "Diterpenes of *Araucaria excelsa*." Phytochemistry, 1972, 11, 839–41.

Caputo, R.; Mangoni, L.; Monaco, P.; Pelosi, L.; Previtera, L. "Neutral diterpenes from *Araucaria bidwilli*." Phytochemistry, 1976, 15, 1401–2.

Cardenas, L.C.; Rodrigez, J.; Rigueza, R.; Chamy, M.M. "Mitrariosides, five bitter labdane glycoside from *Mitraria coccinea* (Gesneriaceae)." Liebigs Ann. Chem. 1992, 665–8.

(Continued)

*Primary Examiner*—Gollamudi S. Kishore
(74) *Attorney, Agent, or Firm*—Jones Day

(57) ABSTRACT

The present invention relates to novel compositions based on hydrated lipidic lamellar phases or liposomal compositions, prepared by combining different lipid molecules, synthetic and/or from natural sources, said compositions comprising at least one of a) labd-13-ene-8α, 15-diol and/or derivatives thereof; b) labd-14-ene-8, 13-diol or derivatives thereof; c) 3β-hydroxy-labd-14-ene-8, 13-epoxy and/or derivatives thereof, d) a plant extract containing the aforementioned labdanes or derivatives thereof. The compositions of the invention exhibit cytotoxicity against cancerous cells and are utilized for the treatment of tumors and leukemias.

40 Claims, No Drawings

OTHER PUBLICATIONS

Carman, R.M. "Optical rotation and structure in the labdane series of diterpenoids." Aust. J. Chem., 1966, 19, 629–42.
Carman, R.M.; Craig, W.J.; Shaw, I.M. "Diterpenoids. XXXI. Three new resin acids." Aust. J. Chem., 1973, 26, 209–14.
Casadevall et al. "Contraction de cycle a partir de la tosyloxy–8 bicyclo[4.2.0]octanone–7 cis." Tetrahedron, 1975, 31, 757–63 (in French with English abstract).
Chen, TC; Hinton, DR; Zidovetski, R; Hoffman, FM. "Up–regulation of the cAMP/PKA pathway inhibits proliferation, induces differentiation, and leads to apoptosis in malignant gliomas." Lab. Invest., 1998 78(2), 165–74.
Chinou, I.; Demetzos, C.; Harvala, C.; Roussakis, C.; Verbist, J.F. "Cytotoxic and antibacterial labdane–type diterpenes from the aerial parts of *Cistus incanus* subsp. *creticus*." Planta Med., 1994, 60, 34–6.
Colletta, G; Girafici, AM; Consiglio, E; Vecchio, G. "Forskolin and a tumor promoter are able to induce c–fos and c–myc expression in normal, but not in a v–ras–transformed rat thyroid cell line." Oncogene Res, 1987, 1(4), 459–66.
Cunningham, A.; Martin, S.S.; Langenheim, J.H. "Resin acids from two amazonian species of *Hymenaea*." Phytochemistry, 1973, 12, 633–5.
Darias, V.; Bravo, L.; Rabanal, R.; Sanchez–Mateo, C.C.; Martin–Herrera, D.A. "Cytostatic and antibacterial activity of some compounds isolated from several lamiaceae species from the Canary Islands." Planta Med., 1990, 56, 70–72.
De Pascual, T.; Urones, J.G.; Mateos, F.G. "Terpenoides monohidroxilados de la gomorresina de *Cistus Ladaniferus L.*" Ann. Quim., 1977, 73, 1024–8 (in Italian with English summary).
De Pascual, T.; Urones, J.G.; Marcos, I.S.; Nunez, L.; Basabe, P. "Diterpenoids and flavonoids from *Cistus palinhae*." Phytochemistry, 1983, 22, 2805–8.
De Pascual, T.; Bellido I.S.; Basade, P.; Marcos, I.S.; Ruano, L.F.; Urones, J.G. "Labdane diterpenoids from *Cistus labdaniferus*." Phytochemistry, 1982, 21, 899–901.
Demetzos, C.; Harvala, C.; Phillianos, S.M.; Skaltsounis, A.L. "A new labdane–type diterpene and other compounds from the leaves of *Cistus incanus* ssp. *cretus*." J. Nat. Prod., 1990, 53, 1365–68.
Detmetzos, C.; Mitaku, S.; Couladis, M.; Harvala, C.; Kokkinopoulos, D. "Natural metabolites of ent–13–epi–manoyl oxide and other cytotoxic diterpenes from the resin "LADANO" of *Cistus creticus*." Planta Med., 1994, 60, 590–591.
Demetzos, C.; Mitaku, S.; Skaltsounis, A.L.; Couladis, M.; Harvala, C.; Libot, F. "Diterpene esters of malonic acid from the resin "LADANO" of *Cistus creticus*." Phytochemistry, 1994, 35, 979–81.
Demetzos, C.; Stahl, M.; Anastassaki, T.; Gazouli, M.; Tzouvelekis, L.; Rallis, M. "Chemical analysis and antimicrobial activity of the resin ladano, or its essential oil and of the isolated compounds." Planta Med., 1998, 65, 76–78.
Dimas K.; Demetzos, C.; Marsellos, M.; Sotiriadou, R.; Malamas, M.; Kokkinopoulos, D. "Cytotoxic acttivity of labdane type diterpenes against human leukemic cell lines in vitro." Planta Med., 1998, 64, 208–11.
Dimas, K.; Demetzos, C.; Mitaku, S.; Marsellos, M.; Tzavaras, T.; Kokkinopoulos, D. "Cytotoxic activity and antiproliferative effects of a new semi–synthetic derivative of ent–13β–hydroxy–13–epi–manoyl oxide on human leukemic cell lines." Anticancer Res., 1999, 19, 4065–72.
Dimas, K; Kokkinopoulos, D; Demetzos, C; Marselos, M; Sotiriadou, R; Malamas, M. "The effect of sclareol on growth and cell cycle progression of human leukemic cell lines." Leukemia Res., 1999, 23; 217–34.
Fernandez, C.; Fraga, M.B.; Hernandez, C.M. "Diterpenes from *Sideritis nutans*." Phytochemistry, 1986, 25, 2825–27.
Fukuyama, Y.; Yokoyama, R.; Ohsaki, A.; Takahashi, H.; Minami, H. "An example of the co–occurrence of enantiomeric labdanetype diterpenes in the leaves of *Mimosa hostilis*." Chem. Pharm. Bull., 1999, 47, 454–5.
Fullas, F; Houssain, RA; Chai, HB; Pezzuto, JM; Soejarto, DD; Kinghorn, AD. "Cytotoxic constituents of *Baccharis gaudichaudiana*." J. Nat. Prod., 1994, 57(6), 801–807.
Galli, C; Meucci, O; Scorziello, A; Werge. TM; Calissano, P, Schettini, G. "Apoptosis in cerebellar granule cells is blocked by high KCI, forskolin, and IGF–1 through distinct mechanisms of action: the involvement of intracellular calcium and RNA synthesis." J. Neurosci., 1995, 15(20), 1172–1179.
Garcia–Granados, A.; Martinez, A.; Molina, A.; Onorato, M.E.; Rico, M.; Saez de Buruaga, A.; Saez de Buruaga, J.M. "Diterpenoids from *Sideritis varoi* subspecies *cuatrecasasii:* $^{13}$C NMR of ent–13–epi–manoyl oxides functionalized at C–12." Phytochemistry, 1985, 25, 1789–93.
Gonzalez, A.G.; Fraga, B.M.; Hernandez, M.G.; Larruga, F.; Luis, J.G. "Four new labdane diterpene oxides from *Sideritisgomerae*." Phytochemistry, 1975,14, 2655–6.
Hanson, J.R. "Diterpenoids." Terpenoids and Steroids. A specialist Periodical Report, The Chemical Society: Burlington House, London, 1976.
Hanson, J.R. "Diterpenoids." Natural Prod. Reports, 1989, 8, 1.
Harlem, D.; Khoung–Huu, F. "Chemistry of Larixol.II—hemisynthesis of (–)–borjatriol." Tetrahedron, 1997, 53, 673–80.
Heldin, NE; Paulsson, Y; Forsberg, K; Heldin, CH, Westermark, B. "Induction of cyclic AMP synthesis by forskolin is followed by a reduction in the expression of c–myc messenger RNA and inhibition of $^{3}$H–thymidine incorporation in human fibroblasts." J Cell. Physiol., 1989, 138(1), 17–23.
Irie, H.; Miyashita, M.; Kouno, I.; Hamanaka, N.; Sugioka, M. "Cunninghamic acids A and B, novel bis(labdane)–type diterpenoids from *Cunninghamia lanceolata*." Tetrahedron Lett., 1992, 33, 5761–2.
Itokawa, H; Morita, H; Katou, I; Takeya, K; Cavalheiro, AJ; Oliveir, RCB; Ishige, M; Motodime, M. "Cytotoxic diterpenes from the rhizomes of *Hedychium coronarium*." Planta Med, 1988, 311–315.
Iwagawa, T.; Yaguchi, S.; Hase, T.; Okubo, T.; Kim, M. "Gomojosides, labdane diterpenoids from *Viburnum suspensum*." Phytochemistry, 1992, 31, 1311–15.
Jakupovic, J.; Schuster, A.; Wasshausen, D.C. "Acetylenes and labdanes from *Baccharis pedunculata*." Phytochemistry, 1991, 30, 2785–87.
Jolad, S.D.; Timmermann, B.N.; Hoffman, J.J.; Bates, R.B.; Siahaan, T.J. "Havardic acids A–F and havardiol, labdane diterpenoids from *Grindelia havardii*." Phytochemistry, 1987, 28, 483–9.
Kalpoutzakis, E.; Chinou, I.; Mitaku, S.; Skaltsounis, A.L.; Harvala, C. "Antibacterial labdane–type diterpenes from the resin "LADANO" of *Cistus creticus* subsp. *creticus*." Natural Product Letters, 1998, 11, 173–9.

Kamata, H; Tanaka, C; Yasigawa, H; Hirata, H. "Nerve growth factor and forskolin prevent $H_2O_2$–induced apoptosis in PC12 cells by glutathione independent mechanism." Neurosci. Lett., 1996, 212(3), 179–82.

Keren–Tal, I; Suh, BS, Dantes, A; Lindner, S; Oren, M; Amsterdam, A. "Involvement of p53 expression cAMP–mediated apoptosis in immortalized granulosa cells." Exp. Cell Res., 1995, 218(1), 283–95.

Lawrence, B.M. "Progress in essential oils." Perfumer and Flavorist, 1986, 11, 111.

Lopez, M.A.; von Carstenn–Lichterfelde, C.; Rodriguez, B.; Fayos, J.; Martinez–Ripoli, M. "Andalusol, a new diterpenoid from a *Sideritis arborescens* Salzm. subspecie. Chemical and X–ray structure determination." J. Org. Chem. 1977, 42, 2517.

Lopez de Lerma, J.; Garcia–Blanco, S.; Rodriguez, J.G. "New compounds from *Ballota hispanica*. X–ray crystal and molecular structure of hispanonic acid methyl ester (MEAH)." Tetrahedron Lett., 1980, 1273–74.

Machwate, M; Rodan, SB; Rodan, GA, Harada, SI. "Sphingosine kinase mediates cyclic AMP suppression of apoptosis in rat periosteal cells." Mol. Pharmacol. 1998, 54(1), 70–77.

Malochet–Grivois, C; Roussakis, C; Robillard, N; Biard, JF, Riou, D; Debitus, C; Verbist JF. "Effects in vitro of two marine substances, chlorolissoclimide and dichlorolissoclimide, on a non–small–cell bronchopulmonary carcinoma line (NSCLC–N6)." Anticancer Drug Des., 1992, 7(6), 493–502.

Matsuda, T; Kuroyanagi, M; Sugiyama, S; Umehara, K; Ueno, A; Nishi, K. "Cell differentiation–inducing diterpenes from *Andrographis paniculata* NEES." Chem. Pharm. Bull. 1994, 42(6), 1216–25.

McChesney, J.D.; Kunzi, S.A. "Microbial models of mammlian metablism: Sclareol metabolism." Planta Med., 1990, 56, 693.

Miyamoto, K; Matsanuga, T; Koshiura, R; Tagaki, K; Satake T; Hasegawa, T. J. "Comparative studies on the combined cytotoxic effect of forskolin with mitomycin C and responsiveness to forskolin in rat ascites hepatoma AH66 cells and AH66F cells." Pharmacobiodyn. 1987, 10(7), 346–352.

Morita, H; Itokawa, H. "Cytotoxic and antifungal diterpenes from the seeds of *Alpinia galanga*." Planta Med. 1988, 54, 117–120.

Munesada, K.; Siddiqui, H.L.; Suga, T. "Biologically active labdane–type diterpene glycosides from the root–stalks of *Gleichenia japonica*." Phytochemistry, 1992, 31, 1533–6.

Nortin, T. "Review Article. Some aspects of the chemistry of the order pinales." Phytochemistry, 1972, 11, 1231–42.

Oda, T; Komatsu, N; Muramatsu, T. "Inhibitory effect of dideoxyforskolin on cell death induced by ricin, modeccin, diphtheria toxin, and *Pseudomonis* toxin in MDCK cells." Cell. Struct. Funct., 1997, 22(50), 545–554.

Ohloff, G. "Chapter 15. The fragrance of Ambergris." Fragrance Chemistry: The science of the sence of smell, Academic Press, Inc.: New York, 1982, pp. 535–573.

Ohtani, K.; Yang, C.; Miyajima, C.; Zhou, J.; Tanaka, O. "Labdane0type diterpene glycosides from fruits of *Rubus foliolosus*." Chem. Pharm. Bull. 1991, 29, 2443–5.

Oztunc, A.; Imre, S.; Latter, H.; Wagner, H. "Ent–13–epiconcinndiol from the red alga *Chonddria tenuissima* and its absolute configuration." Phytochemistry, 1989, 28, 3403–4.

Prakash, O.; Bhakuni, D.S.; Kapil, R.S.; Subba, G.S.R.; Ravindranath, B. "Diterpenoids of *Roylea calcina* (Roxb.) briq." J. Chem. Soc. Perkin I. 1979, 1305–8.

Rice, RH; LaMontagne, AD; Petito, CT; Rong, XH. "Differentiation of cultured epithelial cells: response to toxic agents." Environ. Health Perspect., 1989, 80, 239–246.

Rodriguez, B.; Sanova, G. "Diterpenoids from *Galeopsis angustifolia*." Phytochemistry, 1980, 19, 1805–7.

Shenker, BJ; Matt, WC. "Suppression of human lymphocyte responsiveness by forskolin reversal by 12–O–tetradecanoyl phorbol 13–acetate, diacylglycerol and ionomycin." Immunopharmacology, 1987; 13(1), 73–86.

Singh, M.; Pal, M.; Sharma, R.P. "Biological activity of the labdane diterpenes." Planta Med., 1999, 65, 2–8.

Stipanovic, R.D.; O'Brien, D.H.; Rogers, C.E.; Thompson, T.E. "Diterpenoid acids, (–)–cis– and (–)–trans–ozic acid, in wild sunflower, *Helianthus*." J. Agric. Food. Chem., 1979, 27, 458–9.

Tabacik, C.; Bard, M. "Etude chimio–taxonomique dans le genre *Cistus*." Phytochemistry, 1971, 10, 3093–3106 (in French with English Abstract).

Tajima et al. "Amber odor constituents in labdanum gum." Flavors, Frangrances and Ess. Oils. Proceedings of the 13.sup.th International Congress of Flavours, Fragrances and Essential Oils, Baser et al. Editor. Istanbul, Turkey, Oct. 15–19, 1995 vol. 2, pp. 217–224.

Tahara et al. "$^1$H NMR chemical shift value of the isoflavone 5–hydroxyl proton as a convenient indicator of 6–substitution or 2'hydroxylation." Phytochemistry, 1991, 30, 1683–89.

Torrehegra, R.; Robles, J.; Waibel, R.; Lowel, A.; Achenbach, H. "Diterpenes and diterpene xylosides from *Conyza trihecatactis*." Phytochemistry, 1994, 35, 195–99.

Tsichritzis, F.; Jakupovic, J. "Diterpenes from *Leyssera gnaphaloides*." Phytochemistry, 1991, 30, 211–3.

Uchio, Y.; Nagasaka, M.; Guchi, S.E.; Matsuo, A.; Nakayama, M.; Hayashi, S. Labdane diterpene glycosides with 6–deoxy–L–idose from *Aster spathulifolius Maxim*. Tetrahedron Lett., 1980, 21, 3775–82.

Urones, J.G.; Marcos, I.S.; Martin, D.D.; Alonco, M.C.; Brito, M.S.F.; Rodilla, J.M.L. "Minor labdane diterpenoids from *Halimium verticillatum*." Phytochemistry, 1989, 28, 557–60.

Urones, J.G.; Marcos, I.S.; Basabe, P.; Sexmero, M.J.; Carrillo, H.; Melchor, M.J. "Minor labdane diterpenoids from *Halimium viscosum*." Phytochemistry, 1994, 37, 1359–61.

Wu, C. L. and Asakawa, Y. "Terpenoids of *Pleurozia acinosa*." Phytochemistry, 1988, 27, 940–42.

Zdero, C.; Bohlmann, F.; King, R.M. "Guaianolides and labdanes from *Brickellia* species." Phytochemistry, 1991, 30, 1591–95.

Zdero, C.; Bohlmann, F.; Niemeyer, H.M. "An unusual dimeric sesquiterpene and other constituents from Chilean *Baccharis* species." Phytochemistry, 1991, 30, 1597–1601.

Zdero, C.; Bohlmann, F.; Niemeyer, H.M. "Diterpenes and umbelliferone derivatives from *Haplopappus deserticola*." Phytochemistry, 1990, 29, 326–29.

Zdero, C.; Bohlmann, F.; King, R.M. "Diterpenes and norditerpenes from the *Aristeguetia* group." Phytochemistry, 1991, 30, 2991–3000.

Zdero, C.; Bohlmann, F. "Macrolide diterpenes and other ent–labdanes from *Corymbium villosum*." Phytochemistry, 1988, 27, 227–231.

Zdero, C.; Bohlmann, F.; Mungai, G.M. "Carvotacetone derivatives and other constituents from representatives of the *Sphaeranthus* group." Phytochemistry, 1991, 30, 3297–3303.
Zdero, C.; Bohlmann, F.; Niemeyer, H.M. "Friedolabdanes and other constituents from Chilean *Haplopappus* species." Phytochemistry, 1991, 30, 3669–77.
Zdero, C.; Bohlmann, F. "Ent–labdanes, manolyoxide and helipterol derivatives from *Chrysocephalum ambiguum*." Phytochemistry, 1992, 31, 1631–38.
Zinkel, D.F.; Clarke, W.B. "Resin acids of *Pinus resinosa* needles." Phytochemistry, 1985, 24, 1267–77.
Ostro M.J. "Chapter 9. Liposomes in the diagnosis and treatment of cancer." Liposomes From Biophysics to Therapeutics Ed. by Marc. Ostro Marcel Dekker, 1987, pp 227–338.
Sugarmen S.M. et al. "Liposomes in the treatment of malignancy: a clinical perspective." Critical Reviews in Oncology Hematology vol. 12, pp 231–242, 1992.
Chinou I. et al. "Cytotoxic and antibacterial labdane–type diterpenes from the aerial parts of *Cistus* incanus subsp. *creticus*." Planta Med. 60 p 34–36, 1994.

* cited by examiner-

PHARMACEUTICAL FORMULATIONS COMPRISING LABDANES FOR THE TREATMENT OF TUMORS OR LEUKEMIAS

Matter enclosed in heavy brackets [ ] appears in the original patent but forms no part of this reissue specification; matter printed in italics indicates the additions made by reissue.

BACKGROUND OF THE INVENTION

A very large number of diterpenoids possessing a labdane skeleton (FIG. 1)

Figure 1

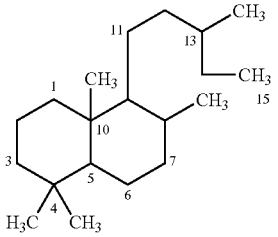

occur in nature (Connoly, J. D.; Hill, R. A Dictionary of Terpenoids, Chapman and Hall: London 1991). The interest in studying labdanes is heightened due to the wide range of biological activities of these compounds (Singh, M.; Pal, M.; Sharma, R. P. Plants Med., 1999, 65, 2–8.). They comprise a decalin system and a C-6 ring, which may be open or closed with an oxygen atom, as in manoyl oxide and its derivatives. Labdanes have been isolated from several plant families, such as Asteraceae, Labiateae, Cistacease, Pinaceae, Cupressaceae, Taxodiaceae, Acanthaceae, Annonaceae, Caprifoliaceae, Solanaceae, Apocynaceae, Verbenaceae and Zingiberaceae. In addition they have been isolated from marine algae of the genus Laurence, from Taonia atomaria and from the red alga Chondria tenuissima.

The conifers are an important source of diterpenoids. Several labdanes have been detected in the neutral fraction of the oleoresin of Araucaria excelsa, including manool as well as nor-labdanes (Caputo, R.; Mangoni, L.; Monaco, P. Phytochemistry, 1972, 11, 839–840). A variety of biological activities have been associated with labdane diterpenes including antibacterial, antifungal, antiprotozoal, enzyme induction, anti-inflammatory modulation of immune cell functions, as well as cytotoxic and cytostatic effects against human leukemic cell lines. (k. Dimas et al. Planta Med. 1998, 208–211; K. Dimas et al. Leukemia Res. 1999, 4065–4072). In addition to the (antimicrobial, enzyme and endocrine related) properties mentioned above, it is interesting that many labdane type diterpenes also exhibit significant properties against cancer cells. A number of labdane type diterpenes tested exhibited remarkable antiproliferative and cytotoxic activities (Itokawa, H. et all. Planta Med. 1988, 311–315; K. Dimas et al. Planta Med. 1998, 208–211; K. Dimas et al. Leukemia Res. 1999, 217–234; K. Dimas et al. Anticancer Res. 1999, 4065–4072).

Labdane furanoids, and forscolin derivatives are the subject of several patents and applications, including European Patent Application 93103605.7; International Patent Publication No. WO 97/45099; International Patent Publication No. WO 91/02525; and International Patent Publication No. WO 85/03637.

Liposomes, or phospholipid vesicles, are self-assembled colloidal particles that occur naturally and can be prepared artificially (Lasic, D. D. Liposomes: from Physics to Applications. Elsevier), as shown by Bangham and his students in the mid-1960s (Bangham, A. D. ed. (1983) Liposomes Letters, Academic Press). At first, they were used to study biological membranes; several practical applications, most notably in drug delivery, emerged in the 1970s. Today, they are a very useful model, reagent and tool in various scientific disciplines, including mathematics and theoretical physics, biophysics, chemistry, colloid science, biochemistry and biology. Liposomes were introduced as drug-delivery delivery vehicles in the 1970s. Early results were, however, rather disappointing, owing mainly to their colloidal and biological instability, and their inefficient and unstable encapsulation of drug molecules. Their utility was improved following basic research that increased our understanding of their stability and interaction characteristics.

In the scientific literature, there is reference to a great number of liposomic pharmaceutical forms. Many of these are in the clinical study stage and some other have been already registered and marketed. Among the medicines formulated in liposomic form, are econazole, amfotericin B, minoxidyl and some anticancer and antiviral medicines, which are in the clinical study stage.

DETAILED DESCRIPTION OF THE INVENTION

It has been found that naturally occurring labdanes, such as labd-13-ene-8α, 15-diol, labd-14-ene-8, 13-diol, and 3β-hydroxy-labd-14-ene-8, 13-epoxy, exhibit biological properties in their pure state (Dimas et al., Planta Med. 1998) and may be useful as novel pharmaceutical and medicinal agents. The present invention deals with preparation of hydrated lipidic lamelar phases or liposomes particularly conventional and/or PEGylated and/or protein conjugated, containing the above compounds and their derivatives or plant extracts containing them, which are part of this invention. The compositions of the invention are useful for the treatment of neoplastic diseases.

As used herein the term "alkyl" refers to a straight or branched, saturated hydrocarbon containing from one to about twelve carbon atoms such as, for example, methyl, ethyl, n-propyl, i-propyl, n-butyl, s-butyl and t-butyl, wherein one or more of the hydrogen atoms may be substituted.

As used herein the term "alkenyl" refers to a straight or branched hydrocarbon containing from one to about twelve carbon atoms where at least one carbon-carbon bond is unsaturated such as for example, vinyl, allyl, and butenyl, wherein one or more of the hydrogen atoms may be substituted.

As used herein the term "alkynyl" refers to a straight or branched hydrocarbon containing from one to about twelve carbon atoms where at least one carbon-carbon bond is doubly unsaturated such as for example, acetylene, propynyl and butynyl, wherein one or more of the hydrogen atoms may be substituted.

As used herein the term "cycloalkyl" refers to a cyclic hydrocarbon containing from three to about twelve carbon atoms such as, for example, cyclopropyl, cyclobutyl, cyclopentyl and cyclohexyl, wherein one or more of the hydrogen atoms may be substituted.

As used herein the term "aralkyl" refers to a straight or branched, saturated hydrocarbon containing from one to about twelve carbon atoms, which is substituted with an aromatic ring such as, for example, benzyl and phenethyl, wherein one or more of the hydrogen atoms may be substituted.

As used herein the term "heterocyclyl" refers to a cyclic hydrocarbon, wherein at least one carbon atom has been replaced by a heteroatom such as, for example, nitrogen, oxygen or sulfur, containing from three to about twelve atoms such as, for example, furan, pyran and imidazole.

As used herein the term "dialkylaminoalkyl" refers to a straight or branched saturated hydrocarbon containing from one to about twelve carbon atoms, which is connected to a tertiary amino group containing two alkyl groups such as, for example, diethylaminoethyl. Preferably, the dialklyaminoalkyl group is present as the acid addition salt resulting from reaction with either an inorganic or organic acid.

As used herein the terms "alkylthioketones", "alkenylthioketones", "alkynylthioketones", "cycloalkylthioketones", "aralkylthioketones" and "heterocyclothioketones" refer to a thioketone connected to a further radical.

As used herein the terms "alkylcarbonyl", "alkenylcarbonyl", "alkynylcarbonyl", "cycloalkylcarbonyl" and "aralkylcarbonyl" refer to a carbonyl connected to a further radical.

As used herein the term "sugars" refers hexoses or pentoses in their pyranose or furanose state or disaccharides containing hexose-hexose, pentose-pentose, hexose-pentose or pentose-hexose in their pyranose or furanose state. These sugars may be substituted with amino or halogen groups, preferably chlorine, bromine or iodine.

1. Labdanes of the Invention

The labdanes of the present invention include:

A. Formula I,

LABD-1-ENE-8α,15-DIOL (I)

I

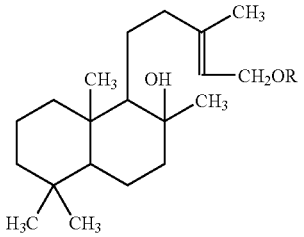

Wherein R wherein R is selected from the group consisting of H, alkylcarbonyl, alkenylcarbonyl, alkynylcarbonyl, cycloalkylcarbonyl, aralkylcarbonyl, alkyl, alkenyl, alkynyl, cycloalkyl, aralkyl, dialkylaminoalkyl, alkylthioketones, alkenylthioketones, alkynylthioketones, cycloalkylthioketones, aralkylthioketones, heterocyclylthioketones and sugars.

B. Formula II

LABD-14-ENE-8,13-DIOL (II)

II

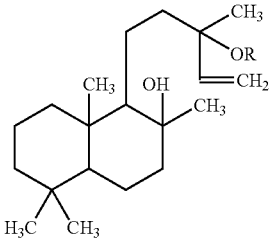

Wherein R is selected from the group consisting of H, alkylcarbonyl, alkenylcarbonyl, alkynylcarbonyl, cycloalkylcarbonyl, aralkylcarbonyl, alkyl, alkenyl, alkynyl, cycloalkyl, aralkyl, dialkylaminoalkyl, alkylthioketones, alkenylthioketones, alkynylthioketones, cycloalkylthioketones, aralkylthioketones, heterocyclylthioketones and sugars.

C. Formula III

3β-HYDROXY-LABD-14-ENE-8,13-EPOXY

III

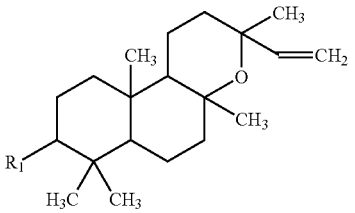

Wherein $R_1$ is =O, $OR_2$ or a halogen selected from the group consisting of chlorine, bromine or iodine. $R_2$ is selected from the group consisting of H, alkylcarbonyl, alkenylcarbonyl, alkynylcarbonyl, cycloalkylcarbonyl, aralkylcarbonyl, alkyl, alkenyl, alkynyl, cycloalkyl, aralkyl, dialkylaminoalkyl, alkylthioketones, alkenylthioketones, alkynylthioketones, cycloalkylthioketones, aralkylthioketones, heterocyclylthioketones and sugars.

For the above derivatives, when R or $R_2$ is dialkylaminoalkyl, the diethylaminoethyl group is preferred and a suitable acid addition salt is derived from inorganic or organic acid i.e hydrochloride, hydrobromide, sulfate, phosphate, acetate, oxalate, tartrate, citrate, maleate or fumarate. When R or [$R^2$] $R_2$ is aralkyl, phenylalkyl groups can be substituted by 1, 2 and 3 identical or different substituents such as halogen, C1–C3-alkyl, C1–C3-alkoxy, hydroxy, nitro, amino, trifluoromethyl, cyano and azodo.

In addition to the optical centers of the labdane nucleus, the substituents may also have chiral centers, which contribute to the optical properties of the compounds to the invention. This invention embraces all the optical isomers and racemic forms of the compounds according to the invention where such compounds have chiral centers in addition to those of the labdane nucleus.

Preferably, the labdanes used to prepare the compositions of the invention are isolated and/or purified labdanes. The labdanes of the invention may be at least 70% pure, 80% pure, 90% pure, 95% pure, 99% pure or 99.5% pure, as well as 100% pure. By "pure," it is meant that the labdane is free from other compounds, thus, a 70% pure labdane preparation is one in which the labdane comprises 70%, by weight, of the total preparation.

The labdanes, labd-13-ene 8α,15-diol (I) and its derivative labd-13-ene 8α,15-yl acetate as well as 3β-substituted -labd-14-ene-8,13-epoxy when 3-substitue is hydroxy (OH) (III) or acetoxy (O Ac) groups have been detected into the extracts and essential oils of the plant Cistus creticus subsp. eriocephalus, and then identified for the first time (Anastassaki, Demetzos et al. Planta Med. 1999 735–739) using GC-MS (Gas Chromatography-Mass Spectrometry) methodology. The above compounds have been isolated in their pure state and their structures have been determined using spectroscopic methods, mainly NMR (Nuclear Magnetic Resonanse) (Demetzos et al. unpublished data). The labdane, labd-14-ene-8,13-diol (II) namely sclareol has been isolated from Clary sage (Salvia sclarea Linn), as well as from Cistus incanus subsp. creticus (Ulubelen A., et al. Phytochemistry 1985, 1386; Demetzos C., Ph. D Thesis, Athens 1990).

2. Liposome Preparation

The present invention provides liposomal formulations comprising one or more of the above described compounds. Any liposomal formulation known to those of skill in the art may be applied to the above described labdane compounds.

The lipids useful for the preparation of hydrated lipidic lamelar phases of liposomes comprising labdanes and/or their derivatives are described. The lipid molecules may be, but are not limited to, naturally occurring lipids such as HSPC (hydrogenated soy phosphatidylcholine), EPC (a mixture of saturated and unsaturated lipids from eggs) SPS (soy phosphatidylserine as sodium salt) and lipids isolated from natural sources (i.e. plants, marine organism and animal tissues) as mixtures of lipids and some synthetic lipids like: DSPC (distearoylphosphatidylcholine), DMPC (dimyristoylphosphatidylcholine) and DPPC (dipalmtoylphsophatidylcholine) DOPC (dioleoylphosphatidylcholine), which are saturated esters of phosphatidylcholine. Polyethylene glycol (PEG)-lipid conjugates have been used to improve circulation times for liposomes cocapsulated drugs and may be used in compositions of the present invention.

PEG-PE(phosphatidylethanolamine) have been used for preparing long circulating liposomes, and may be used in the compositions of the invention. PEG-lipid conjugates may also be used. Examples of PEG-lipid conjugates include 1,2-Diacy-sn-glycero-3-Phosphoethanolamine-N-[Methoxy (Polyethylene Glycol)-2000], in which the term acyl represents myristoyl, palmitpoyl, stearoyl and oleoyl groups.

Conventional or PEGylated liposomes containing cholesterol or cholic acid (transferosomes) in various concentrations by combining different phospholipids may also be utilized in the compositions of the invention. Cholesterol may regulate the stability of liposomes and therefore the inclusion of cholesterol in liposomes may be beneficial for the controlled release of the liposomes associated compounds, such as the labdanes of the present invention. Because of the prolonged circulation in blood and enhanced stability due to steric stabilization by surface-grafted polymers, the polymer-coated long-circulating liposomes have been referred to as sterically stabilized liposomes (Papahadjopoulos, D. et al. (1991) Proc. Natl. Acad. Sci. U.S.A. 88. 11460–11464). The optimal stability of this type of liposome is obtained at around 5 mol % of PEG-lipid (PEG molecular weight 2000 Da (Lasic, D. D. (1994) Angew. Chem, Int. Ed. Engl. 33, 1785–1799). Liposomes may be prepared by combining different synthetic lipids or natural lipids isolated from natural sources, such as lipids from plants and/or marine organisms and/or animal tissues. Liposomes may be prepared not only be combining different phospholipids but also by combining phospholipids with different levels of cholesterol and cholic acid (in its salt form).

Immunoliposomes are either conventional or sterically stabilized liposomes, which have specific proteins on their surface acting as recognition centers. Immunoliposomes may be prepared using the noncovalent biotin-avidin method and covalent bonding of proteins with the liposomes surface.

The PE derivatives of PEG with a terminal carbonyl group (Di acyl-PE-PEG-COOH) or with a terminal maleimidyl group (Di acyl-PE-PEG-MaI) may be synthesized according to K. Maruyama et al. B. B. A (1995) 1234, 74–80.

The use of immunoliposomes in the treatment of tumors resulted in a marked improvement in the drugs efficacy not only in comparison to the drug on its own but also compared to conventional liposomes.

Liposomes of different sizes and characteristics require different methods of preparation. The most simple and widely used method for preparation of MLV (Multilamelar Vesicles) is the thin-film hydration procedure in which a thin film of lipids is hydrated with an aqueous buffer at a temperature above the transition temperature of lipids. For lipophilic compounds such as the labdanes and their derivatives part of this invention, the REV (Reverse-Phase Evaporation), techniques is more suitable for the compounds encapsulation. In brief, different MLV liposomes composed of DSPC, DPPC, DMPC, DOPC, Soy Phosphatidylserine as sodium salt with or without cholesterol or cholic acid (as a salt) and PEGylated liposomes with or without cholesterol or cholic acid (as a salt) may be prepared by hydration with a buffer such as TES (N-tris-[hydroxymethyl]methyl 2-amino ethanesulfonic acid), MES 2-[N-morpholino] ethanesulfonic acid], HEPES (N-[2-hydroxyethyl]-piperazine-N-2-ethanesulfonic acid), after the removal of the organic solvent (Chloroform) in which labdanes and their derivatives have been dissolved.

The removal of the organic solvent in vacuum or under an inert gas results in the hydration of the lipids which form into multilayer liposomes upon vigorous shaking of the lipid film in an aqueous solution. The lipophilic labdanes incorporate into lipid bilayers, while the hydrophilic derivatives thereof are encapsulated in the liposomes. The aqueous medium used in hydrating the dried lipid film is preferably pyrogen free. The medium preferably contains physiological salt, such as NaCl, sufficient to produce a near-physiologic osmolarity (about 300 mOs).

The liposome dispersion is sized to achieve a size distribution of vesicles in a size range preferably between about 0.1 to 0.5 microns. The sizing serves to eliminate larger liposomes and to produce a defined size range having optimal pharmacokinetic properties. One preferred method for achieving the desired size distribution of liposome sizes is by extrusion of liposomes through a small-pore polycarbonate membrane sizes whose selected pore sizes such as 0.1, 0.2 or 0.4 microns, correspond approximately to the size distribution of liposomes after one or more passes through the membrane. Typically the liposomes are extruded through the membranes several times until the size distribution stabilises (Shokai et al, 1978). The liposomes dispersion is further treated to remove free labdanes, i.e. labdanes which are not intimately associated with the lipid bilayers. The suspension can be pelted by high-speed centrifugation after dilution, leaving free labdanes and very small liposomes in the supernatant. Another method uses gel filtration by molecular sieve chromatography to separate liposomes from free labdanes. Sephadex (G-75) gel filtration was used in order to remove the free labdanes.

In one embodiment, the final encapsulated liposomal labdane dispersion has the following characteristics:

1. Liposome sizes range between about 0.1 to 0.25 microns
2. Liposome-encapsulated labdanes about 80%–90%
3. The dispersion has a lipid concentration of at least 5 mg total lipid/ml, and near physiological osmolarity.

The dispersion may be sterilized by filtration through a conventional 0.22-micron depth filter.

3. Therapeutic Use of The Compositions of the Invention

The formulations of the invention are useful for treating mammalian cancers or conditions related thereto. By "treating" it is meant that the formulations are administered as an aqueous solution, preferably, the present formulations are suitably buffered and isotonic. Furthermore, for parenteral administration, the formulations of the invention should be sterile. An embodiment of the present invention includes a sterilization step. The sterilization may be carried out in several ways, e.g., by using a bacteriological filter, by incorporating sterilizing agents into the composition, by irradiation, or by heating. Sterilization may be effected, for example, by filtration, e.g., through a 0.2 μm pore size filter. Other methods of sterilizing known to those skilled in the art can also be employed. Suitable sterile and non-sterile excipients are commercially available from: EM Industries, Inc., Hawthorne, N.Y.; J. T Baker, Inc., Hayward, Calif.; Spectrum Quality Products, Inc., Gardena Calif.; Fisher Scientific International, Inc., Hampton N.H.; Aldrich Chemical Co., Inc., Milwaukee Wis.; Abbott Laboratories, Inc., North Chicago Ill.; Baxter Healthcare Corporation, Deerfield Ill.; and Amresco, Inc., Cleveland Ohio.

To formulate aqueous parenteral dosage forms for injection, an aqueous medium, e.g., physiological saline or purified water, paclitaxel solubilizers, and any additional components are mixed in sanitized equipment, filtered, and packaged according to well known methods in the art (for a discussion see e.g., Remington's Pharmaceutical Sciences, Alfonso R. Gennaro ed., Mack Publishing Co. Easton, Pa., 19th ed., 1995, Chapter 87). A formulation of the invention can be prepared in sterile form, such as a sterile solid, liquid, semisolid, gel, suspension, emulsion, or solution, preferably, as a sterile liquid concentrate that can be dissolved or dispersed in a sterile aqueous medium or any other injectable sterile medium prior to parenteral administration.

To formulate and administer transdermal dosage forms, well known transdermal delivery mediums such as lotions, creams, and ointments and transdermal delivery devices such as patches can be used (Ghosh, T. K.; Pfister, W. R.; Yum, S. I. Transdermal and Topical Drug Delivery Systems, Interpharm Press, Inc. p. 249–297, incorporated herein by reference). For example, a reservoir type patch design can comprise a backing film coated with an adhesive, and a reservoir compartment comprising a formulation of the invention, that is separated from the skin by a semipermeable membrane (e.g., U.S. Pat. No. 4,615,699, incorporated herein by reference). The adhesive coated backing layer extends around the reservoir's boundaries to provide a concentric seal with the skin and hold the reservoir adjacent to the skin.

Gels, semisolids, and solid forms, containing the active can be prepared according to well known methods. For instance, by mixing in a standard V-blender, preferably, under anhydrous conditions. The homogeneous mixture can be passed through a screen mesh if desired. A comprehensive discussion on formulating solid forms is presented in Remington's Pharmaceutical Sciences, Alfonso R. Gennaro ed., Mack Publishing Co. Easton, Pa., 19th ed., 1995, Chapter 92, incorporated herein by reference.

The dosage form of the invention may be provided in single-unit dose container forms or multi-unit-dose container forms by aseptically filling suitable containers with the sterile solution to a prescribed active content as described above. It is intended that these filled containers will allow rapid dissolution of the composition upon reconstitution with appropriate sterile diluents in situ, giving an appropriate sterile solution of desired active concentration for administration. As used herein, the term "suitable containers" means a container capable of maintaining a sterile environment, such as a vial, capable of delivering a vacuum dried product hermetically sealed by a stopper means. Additionally, suitable containers implies appropriateness of size, considering the volume of solution to be held upon reconstitution of the vacuum dried composition; and appropriateness of container material, generally Type I glass. The stopper means employed, e.g., sterile rubber closures or an equivalent, should be understood to be that which provides the aforementioned seal, but which also allows entry for the purpose of introduction of diluent, e.g., sterile Water for Injection, USP, Normal Saline, USP, or 5% Dextrose in Water, USP, for the reconstitution of the desired active solution. These and other aspects of the suitability of containers for pharmaceutical products such as those of the invention are well known to those skilled in the practice of pharmaceutical arts.

The present invention will be further understood by reference to the following non-limiting examples. The following examples are provided for illustrative purposes only and are not to be construed as limiting the invention's scope in any manner.

EXAMPLES

Example 1

Labd-13-end,8α-ol,15-yl Acetate

Labd-13-end,8α,15 diol (I) (50 mg) was dissolved in 2 ml of Ac2O-Py (acetic anhydrate-pyridine) for 48 hours at room temperature. The reaction mixture evaporated in vacuum to remove the solvents The purity as well the identification of the compound labd-13-ene,8α-ol,15-yl acetate was tested by TLC (Thin Layer Chromatography) and GC-MS (Gas Chromatography-Mass Spectrometry), using chromatography data. Compound was obtained in its pure state (47 mg).

Example 2

Labd-13-ene-8α-ol 15-yl-β(or -α)-D (or -L)-pyrano (or furano)sides as Monosaccharides or as Disaccharides Labd-14-ene-8α-ol 13-yl-β(or -a)-D (or -L)-pyrano (or furano)sides as monosaccharides or as disaccharides. 3-yl-β(or -a)-D (or -L)-pyrano (or furano)sides as monosaccharides or as disaccharides, Labd-14-ene, 8, 13-epoxy As an example Condensation of Labd-13-ene-8α,15-diol (I) with 2,3,4, 6-tetra-O-acetyl-a-D-glucopyranosyl bromide was carried out in a two-phase system consisting of chloroform-1.25M aqueous potassium hydroxide solution and benzyltriethylammonium bromide as catalyst. After a simple work up, followed by column chromatography, the labdane glycosides glycosides were isolated in 30% yield.

Example 3

Thiomidazolide Derivative of 3β-hydroxy-labd-14-ene-8,13-epoxy

3β-hydroxy-labd-14-ene-8,13-epoxy, was converted to its thiomidazolide (45% yield) by treatment with N,N'-thiocarbonydiimidazole (Rasmunssen, J. R. (1980) J. Org. Chem. 45, 2725–2727).

Example 4

Preparation of Liposomes

Liposomes containing encapsulated or incorporated compounds I, II, III (Formulas I, II, III) and their derivatives, were prepared according to methods previously described (Juliano, R. L., Stamp, D. Biochem. Biophys. Res. Commun. 63, 651 (1975)).

In brief, lipid of 5 mg DMPC was dissolved in organic solvent (i.e chloroform) and then was evaporated under vacuum into the well of glass tube.

Compounds I, II, III (Formulas I, II, III) at I 0% molar ratio were dissolved in chloroform and mixed with the lipid prior to evaporation. In order to form liposomes, 1 ml of iso-osmotic buffer (TES 100 mM+NaCl 100 mM) pH=7.5 and 300 mOs was added to the dried lipid film, and the mixture was dispersed by vortex with continuous temperature control; the usual temperature for preparation of liposomes was 35° C. In order to reduce the size of the liposomes the resultant large vesicles were extruded ten times through an extruder device with polycarbonated membrane with a pore size of 200 nm. The liposomes were passed through Sephadex G-75 to remove the free compound in all cases. The liposomal composition was:

DMPC 10 mg in 2 ml TES 100 mM+NaCl 100 mM.

a. 5 mg DMPC/compound I (formula I) (0.25 mg)

b. 5 mg DMPC/compound II (formula II) (0.25 mg)

c. 5 mg DMPC/compound III (formula III) (0.25 mg)

The drug concentration in all cases was 250 μg/ml

The results showed that into the above composition of liposomes the encapsulation was >80%.The retention of the compounds into this particular liposome formulation was studied and found to be time dependent.

Example 5

Cytotoxic Activity of labd-13-ene-8α,15-diol Encapsulated in Liposomal Carriers

The following pharmacological methods were used for the evaluation of the biological activities of the compounds of the invention.

Cell Cultures

Human cancer cell lines were used for in vitro drug testing. The cells were maintained as exponentially proliferating suspension cultures in RPMI-1640 medium (supplemented with 10% heat inactivated foetal calf serum, 2mM L-Glutamine and 50 μg/ml gentamycin and incubated at 37° C., in a humidified atmosphere with 5% $CO_2$. Peripheral blood mononuclear cells (PBML) were also isolated from normal donors using the Ficoll-Hypaque method and cultured as the cancer cell lines.

Cytotoxic Activity

To determine the cytotoxicity, log-phase cells from each cell line, resting and activated PBML (1×106 cells/ml), were incubated with free compound or liposomal formulation for 48 h, in 96-well flat-bottomed micro plates.

The initial inoculation densities for each cell line are presented in table (1) and were determined taking into account cell mass and growth rate (Monks A., Scudiero, D., Skehan P., Shomaker R., Pauli K., Vistica D., Hose C et al. Feasibility of a High-Flux Anticancer Drug screen using a diverse panel of cultured human tumor cell lines. JNCI 1991; 83(11): 757–766 Paul K D, Shomaker R H, Hodes L, Monks A, Scudiero D A, Rubinstein L., Plowman J and Boyd M R. Tumor Cell Lines: Development of Mean Graph and Compare Algorithm. JNCI 1989; 81(14): 1088–1092). Viability of the cells was assessed by trypan blue dye exclusion, at the beginning of the experiment and was always greater than 98%.

Cells were added at the appropriate inoculation densities in 96-well micro titer plates and preincubated for 24 hours in a moist atmosphere of 5% CO2 in air at 37oC, to allow stabilization prior to addition of the test compounds. To determine their activity, the free compound or liposomal formulation were added at the same time to each cell line. Cultures, where an equivalent amount of DMSO was added, used as controls. After the addition of the test agents the cells were cultured in micro plates for an additional 48 h under the same conditions. Each test agent was inoculated at five concentrations (10−4 to 10−8 M). The activity for each compound on each cell line was determined by the MTT method with modifications. Briefly 4 h before the end of the 48 h incubation period, MTT (3-(4,5-dimethylthiazol-2-yl)-2–5 diphenyl tetrazolium bromide, Sigma-Aldrich) dissolved in PBS (Phosphate buffered saline), was added in the cell cultures to give a final concentration of 50 μg/ml. At the end of the 48 h incubation period, DMSO was added to the wells and the optical density was measured with an ANTHOS HT II Microelisa reader, using a test wavelength of 550 nm.

The data represent the means of experiments done in triplicates and were analyzed using a two-tailed Student's t-test.

Three parameters GI50, TGI and LC50 were estimated using the MTT method. Briefly GI50 is the concentration where 100*(T−T0)/(C−T0)=50 and measures the growth inhibitory power of the test compound. TGI is the concentration of the test agent where 100*(T−T0)/(C−TO)=0 and measures the cytostatic effect. Finally LC50 is the concentration of the drug where 100*(T−TO)/TO=−50 and measures the cytotoxic effect of the drug. At the above formulas used for the calculation of the three parameters, T is the optical density of the test well after a 48 h period of exposure to test compound; TO is the optical density at the time zero (when the drug is added) and C is the optical density of the control well (cells incubated for 48 h with no additives).

Results

The leukemic cell lines CCRF-CEM, MOLT4, HUT78 (T cells), RPMI 8226 (B cell line), HL60 (promyelocytic cell line), K562 (proerythrocytes) and the multi-drug resistant (MDR) cell lines: CCRF-CEM/C2, HL60/MX1 and HL601MX2 were used. All cell lines were grown and tested for viability as described above. Free compounds and encapsulated (as described above) were tested according to the method described under cytotoxic activity (see Biological activity, above). They were also tested for cytotoxicity as described in Biological Activity against normal PBML resting or activated by the addition of 5 μg/ml PHA-P. Results fro free labd-13-ene-8α,15-diol (means of GI50, TGI, LC50) expressed in μM are summarized in Table 1 while of encapsulated in liposomes in Tables 2 and 3.

TABLE 1

| Label-13-ene-8, 15 diol | GI50 | TGI | LC50 |
|---|---|---|---|
| CCRF-CEM | 75.74 | 141.08 | 200 |
| CCRF-CEM/C2 | 42.27 | 74.96 | 107.65 |
| MOLT4 | 32.32 | 76.22 | 120.11 |
| HUT78 | 109.14 | 186 | 200 |
| RPMI 8226 | 42.2 | 80.08 | 117.96 |
| K562 | 87.08 | 159 | 200 |
| HL60 | 47.69 | 69.74 | 91.8 |
| HL60/MX1 | 52.32 | 80.1 | 107.87 |
| HL601/MX2 | 43.81 | 73.14 | 102.48 |
| MEAN | 59.15 | 104.48 | 138.65 |
| PBML (resting) | >>100 | >>100 | >>100 |
| PGML (stimulating) | 66.2 | >>100 | >>100 |

TABLE 2

| Label-13-ene-8, 15 diol, DPPC | GI50 | TGI | LC50 |
|---|---|---|---|
| CCRF-CEM | 28.74 | 52.23 | 75.72 |
| CCRF-CEM/C2 | 19.12 | 46.55 | 73.99 |
| MOLT4 | 24.61 | 52.41 | 80.21 |
| HUT78 | 13.98 | 49.41 | 83.39 |
| RPMI 8226 | 5.48 | 38.72 | 75.54 |
| K562 | 35.30 | 78.84 | 122.39 |
| HL60 | 33.92 | 56.36 | 78.80 |
| HL60/MX1 | 18.54 | 46.17 | 73.79 |
| HL601/MX2 | 0.62 | 17.81 | 61.78 |
| MEAN | 20.03 | 48.72 | 80.62 |

TABLE 3

| Label-13-ene-8, 15 diol, DMPC | GI50 | TGI | LC50 |
|---|---|---|---|
| CCRF-CEM | 28.56 | 51.93 | 75.30 |
| CCRF-CEM/C2 | 5.14 | 10.42 | 55.36 |
| MOLT4 | 29.72 | 54.75 | 79.78 |
| HUT78 | 6.04 | 28.65 | 66.19 |
| RPMI 8226 | 7.98 | 38.20 | 73.70 |
| K562 | 27.24 | 58.60 | 89.95 |
| HL60 | 32.63 | 55.21 | 77.80 |
| HL60/MX1 | 26.18 | 50.87 | 75.57 |
| HL601/MX2 | 1.65 | 8.36 | 49.79 |
| MEAN | 18.35 | 39.66 | 71.49 |

The effect of the above used formulations against the MDR cell lines are summarized in table 4. The Resistant Factor (RF) is defined as follows: GI50 of the MDR daughter cell line/GI50 of the parental cell line. The (−) represents a parental cell line more resistant than the daughter MDR line.

TABLE 4

| RF (GI50) | CCRF CEM/C2 | HL 60/MX1.1 | HL60/MC2 |
|---|---|---|---|
| Label-13-ene-8α, 15 diol | 0.6 | 1.1 | 0.9 |
| /DPPC | 0.6 | <2 | −55 |
| /DMPC | −6 | 1 | −20 |

TABLE 5

| Concentration | Growth Percentages | | |
|---|---|---|---|
| | NCI-H460 (Lung cancer) | MCF-7 (Breast cancer) | SF-268 (CNS cancer) |
| 100 μM | −80 | −89 | −88 |

Example 6

Cytotoxic Activity of labd-14-ene-8,13-diol Encapsulated in Liposomal Carriers Labd-14-ene-8,13-diol was also encapsulated into liposomes as described above and tested as labd-13-ene-8α, 15-diol. Results are presented in the corresponding tables below (Tables 6–10)

TABLE 6

| Label-14-ene-8, 13 diol | GI50 | TGI | LC50 |
|---|---|---|---|
| CCRF-CEM | 35.00 | 60.00 | 85.00 |
| CCRF-CEM/C2 | 29.05 | 52.41 | 75.78 |
| MOLT4 | 31.60 | 54.66 | 77.72 |
| HUT78 | 33.68 | 56.09 | 78.49 |
| RPMI 8226 | 14.94 | 42.84 | 70.73 |
| K562 | 35.58 | 57.45 | 79.33 |
| HL60 | 41.48 | 60.72 | 79.95 |
| HL60/MX1 | 42.94 | 61.90 | 80.86 |
| HL601/MX2 | 31.41 | 54.12 | 76.83 |
| MEAN | 32.85 | 55.58 | 78.30 |
| PBML (resting) | 34.6 | 63.8 | 93.1 |
| PBML (stimulating) | 33.1 | 61.0 | 89.0 |

TABLE 7

| Label-14-ene-8, 13 diol, DPPC | GI150 | TGI | LC50 |
|---|---|---|---|
| CCRF-CEM | 33.34 | 56.03 | 78.72 |
| CCRF-CEM/C2 | 32.10 | 55.24 | 78.38 |
| MOLT4 | 28.43 | 55.50 | 82.58 |
| HUT78 | 6.22 | 42.52 | 79.81 |
| RPMI 8226 | 5.10 | 45.58 | 82.62 |
| K562 | 55.67 | 113.74 | 171.80 |
| HL60 | 39.50 | 59.98 | 80.46 |
| HL60/MX1 | 7.65 | 33.05 | 66.51 |
| HL601/MX2 | 2.21 | 8.78 | 54.00 |
| MEAN | 23.36 | 52.27 | 86.10 |

TABLE 8

| Label-14-ene-8, 13 diol, DMPC | GI50 | TGI | LC50 |
|---|---|---|---|
| CCRF-CEM | 43.15 | 68.64 | 94.14 |
| CCRF-CEM/C2 | 30.50 | 57.03 | 83.57 |
| MOLT4 | 61.02 | 127.90 | 194.78 |
| HUT78 | 4.18 | 27.78 | 71.43 |
| RPMI 8226 | 37.99 | 67.33 | 96.68 |
| K562 | 53.48 | 105.24 | 157.01 |
| HL60 | 58.12 | 89.87 | 121.62 |
| HL60/MX1 | 37.36 | 75.36 | 113.36 |
| HL601/MX2 | 28.71 | 61.37 | 94.02 |
| MEAN | 39.39 | 75.61 | 114.07 |

TABLE 9

| RF (GI50) | CCRF CEM/C2 | HL 60/MX1.1 | HL60/MC2 |
|---|---|---|---|
| Label-13-ene-8α, 15 diol | 0.8 | 1 | 0.8 |
| /DPPC | 0.97 | −5 | −18 |
| /DMPC | 0.7 | 0.64 | −2 |

Example 7

Cytotoxic Activity of labd-13-ene-8α, 15-yl Acetate

The cytotoxic activity of the derivative of Labd-13-ene-8α, 15-diol i.e. labd-13-ene-8α, 15-yl acetate was also assayed in the same manner as described above (Tables 10–13)

TABLE 10

| Label-13-ene-8, 15-yl acetate | GI50 | TGI | LC50 |
|---|---|---|---|
| CCRF-CEM | 69.09 | 128.17 | 187.00 |
| CCRF-CEM/C2 | 46.77 | 78.83 | 110.88 |
| MOLT4 | 42.80 | 89.95 | 137.10 |
| HUT78 | 95.18 | 164.00 | 200.00 |
| RPMI 8226 | 41.31 | 68.43 | 95.55 |
| K562 | 78.19 | 162.00 | 200.00 |
| HL60 | 44.79 | 67.04 | 89.29 |
| HL60/MX1 | 53.92 | 80.14 | 106.36 |
| HL601/MX2 | 38.78 | 69.90 | 101.03 |
| MEAN | 56.76 | 100.94 | 136.36 |
| PBML (resting) | >>100 | >>100 | >>100 |
| PBML (stimulating) | 65.9 | >>100 | >>100 |

TABLE 11

| Label-13-ene-8, 15-yl acetate, DPPC | GI50 | TGI | LC50 |
|---|---|---|---|
| CCRF-CEM | 31.52 | 53.40 | 75.28 |
| CCRF-CEM/C2 | 37.01 | 58.22 | 79.43 |
| MOLT4 | 32.39 | 56.62 | 80.85 |
| HUT78 | 20.60 | 52.18 | 83.76 |
| RPMI 8226 | 33.97 | 65.74 | 97.52 |
| K562 | 76.94 | 164.92 | 252.91 |
| HL60 | 41.76 | 61.70 | 81.65 |
| HL60/MX1 | 9.60 | 40.58 | 71.56 |
| HL601/MX2 | 8.87 | 40.21 | 71.34 |
| MEAN | 32.52 | 65.95 | 99.37 |

TABLE 12

| Label-13-ene-8, 15-yl acetate, DMPC | GI50 | TGI | LC50 |
|---|---|---|---|
| CCRF-CEM | 31.33 | 53.97 | 76.60 |
| CCRF-CEM/C2 | 19.22 | 46.13 | 73.05 |
| MOLT4 | 29.50 | 55.33 | 81.16 |
| HUT78 | 4.60 | 25.63 | 65.04 |
| RPMI 8226 | 31.93 | 56.59 | 81.24 |
| K562 | 63.86 | 131.28 | 198.70 |
| HL60 | 37.66 | 61.22 | 84.77 |
| HL60/MX1 | 14.17 | 45.20 | 76.23 |
| HL601/MX2 | 23.69 | 49.63 | 75.56 |
| MEAN | 28.44 | 58.33 | 90.26 |

TABLE 13

| RF (GI50) | CCRF CEM/C2 | HL 60/MX1.1 | HL60/MC2 |
|---|---|---|---|
| Label-13-ene-8α, 15-yl acetate | 0.7 | 1.2 | 0.9 |
| /DPPC | 1.15 | −4 | −5 |
| /DMPC | 0.61 | −2.7 | 0.6 |

CONCLUSION

The free and in liposome encapsulated labdanes are cytotoxic against cancer cell lines and are not affected by the multi-drug-resistance phenotype of the cell lines tested. They also exhibit reduced cytotoxicity against normal, resting or activated, human PBML.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A pharmaceutical composition, comprising:

a therapeutically effective amount of at least one compound of Formula 1,

Formula 1

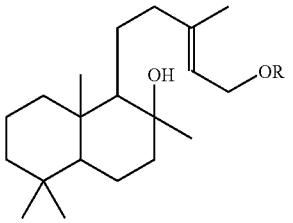

wherein R is selected from the group consisting of H, alkylcarbonyl, alkenylcarbonyl, alkynylcarbonyl, cycloalkylcarbonyl, aralkylcarbonyl, alkyl, alkenyl, alkynyl, cycloalkyl, aralkyl, dialkylaminoalkyl, alkylthioketones, alkenylthioketones, alkynylthioketones, cycloalkylthioketones, aralkylthioketones, heterocyclylthioketones and sugars, wherein the compound of Formula I is encapsulated in the internal part of lipidic lamellar phases or liposomes, or incorporated into lipid bilayers of lipidic lamellar phases or liposomes.

2. The pharmaceutical composition according to claim 1, wherein the pharmaceutical composition is formulated for enteral, parenteral or topical use.

3. The pharmaceutical composition according to any one of claim 1 or 2, wherein the pharmaceutical composition is formulated for treating cancer in a subject having cancer.

4. The composition of claim 1, wherein the lipidic lamellar phases or liposomes comprise one or more phospholipids.

5. The composition of claim 4, wherein the phospholipids are selected from the group consisting of dimyristoylphosphatidylcholine (DMPC), dipalmitoylphosphatidylcholine (DPPC), distearoyl phosphatidylcholine (DSPC), dipalmtoylphosphatidylcholine (DOPC), phosphatidylcholine (PC), and (PEG)-lipid conjugates.

6. The composition of claim 1, wherein the compound of Formula 1 is encapsulated in the internal part of a liposome or incorporated into lipid bilayers of a liposome.

7. The composition of claim 6, wherein the liposomes are about 0.1 to 0.5 microns in diameter.

8. The composition of claim 1, wherein the lipidic lamellar phases or liposomes comprise cholesterol.

9. The composition of claim 1, formulated as a solid.

10. The composition of claim 1, wherein the lipidic lamellar phases or liposomes are dispersed in a pharmaceutically acceptable aqueous diluent.

11. A pharmaceutical composition, comprising:

a therapeutically effective amount of at least one compound of Formula 2,

Formula 2

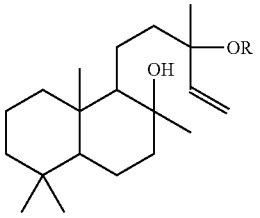

wherein R is selected from the group consisting of H, alkylcarbonyl, alkenylcarbonyl, alkynylcarbonyl, cycloalkylcarbonyl, aralkylcarbonyl, alkyl, alkenyl, alkynyl, cycloalkyl, aralkyl, dialkylaminoalkyl, alkylthioketones, alkenylthioketones, alkynylthioketones, cycloalkylthioketones, aralkylthioketones, heterocyclylthioketones and sugars, wherein the compound of Formula 2 is encapsulated in the internal part of lipidic lamellar phases or liposomes, or incorporated into lipid bilayers of lipidic lamellar phases or liposomes, wherein the lipidic lamellar phases or liposomes comprise one or more phospholipids.

12. A pharmaceutical composition, comprising:

a therapeutically effective amount of at least one compound of Formula 2,

Formula 2

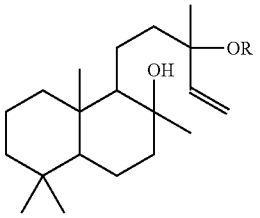

wherein R is selected from the group consisting of H, alkylcarbonyl, alkenylcarbonyl, alkynylcarbonyl, cycloalkylcarbonyl, aralkylcarbonyl, alkyl, alkenyl, alkynyl, cycloalkyl, aralkyl, dialkylaminoalkyl, alkylthioketones, alkenylthioketones, alkynylthioketones, cycloalkylthioketones, aralkylthioketones, heterocyclylthioketones and sugars, wherein the compound of Formula 2 is encapsulated in the internal part of lipidic lamellar phases or liposomes, or incorporated into lipid bilayers of lipidic lamellar phases or liposomes, wherein the lipidic lamellar phases or liposomes comprise cholesterol.

13. The pharmaceutical composition according to any one of claim 11 or 12, wherein the pharmaceutical composition is formulated for enteral, parenteral or topical use.

14. The pharmaceutical composition according to any one of claim 11 or 12, wherein the pharmaceutical composition is formulated for treating cancer in a subject having cancer.

15. The composition of claim 11, wherein the phospholipids are selected from the group consisting of dimyristoylphosphatidylcholine (DMPC), dipalmitoylphosphatidylcholine (DPPC), distearoyl phosphatidylcholine (DSPC), dipalmtoylphosphatidylcholine (DOPC), phosphatidylcholine (PC), and (PEG)-lipid conjugates.

16. The composition of any one of claim 11 or 12, wherein the compound of Formula 2 is encapsulated in the internal part of a liposome or incorporated into lipid bilayers of a liposome.

17. The composition of claim 16, wherein the liposomes are about 0.1 to 0.5 microns in diameter.

18. The composition of claim 11, wherein the lipidic lamellar phases or liposomes comprise cholesterol.

19. The composition of any one of claim 11 or 12, formulated as a solid.

20. The composition of any one of claim 11 or 12, wherein the lipidic lamellar phases or liposomes are dispersed in a pharmaceutically acceptable aqueous diluent.

21. A pharmaceutical composition, comprising:

a therapeutically effective amount of at least one compound of Formula 3,

III

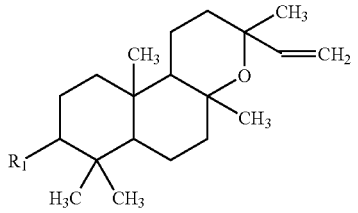

wherein $R^1$ is selected from the group consisting of =O, $OR_2$, or a halogen selected from the group consisting of chlorine, bromine or iodine, and wherein $R_2$ is selected from the group consisting of H, alkylcarbonyl, alkenylcarbonyl, alkynylcarbonyl, cycloalkylcarbonyl, aralkylcarbonyl, alkyl, alkenyl, alkynyl, cycloalkyl, aralkyl, dialkylaminoalkyl, alkylthioketones, alkenylthioketones, alkynylthioketones, cycloalkylthioketones, aralkylthioketones, heterocyclylthioketones and sugars, wherein the compound of Formula 3 is encapsulated in the internal part of lipidic lamellar phases or liposomes, or incorporated into lipid bilayers of lipidic lamellar phases or liposomes.

22. The pharmaceutical composition according to claim 21, wherein the pharmaceutical composition is formulated for enteral, parenteral or topical use.

23. The pharmaceutical composition according to any one of claim 21 or 22, wherein the pharmaceutical composition is formulated for treating cancer in a subject having cancer.

24. The composition of claim 21, wherein the lipidic lamellar phases or liposomes comprise one or more phospholipids.

25. The composition of claim 24, wherein the phospholipids are selected from the group consisting of dimyristoylphosphatidylcholine (DMPC), dipalmitoylphosphatidylcholine (DPPC), distearoyl phosphatidylcholine (DSPC), dipalmtoylphosphatidylcholine (DOPC), phosphatidylcholine (PC), and (PEG)-lipid conjugates.

26. The composition of claim 21, wherein the compound of Formula 3 is encapsulated in the internal part of a liposome or incorporated into lipid bilayers of a liposome.

27. The composition of claim 26, wherein the liposomes are about 0.1 to 0.5 microns in diameter.

28. The composition of claim 21, wherein the lipidic lamellar phases or liposomes comprise cholesterol.

29. The composition of claim 21, formulated as a solid.

30. The composition of claim 21, wherein the lipidic lamellar phases or liposomes are dispersed in a pharmaceutically acceptable aqueous diluent.

31. A method of treating a subject having cancer comprising administering to the patient an amount of the pharmaceutical composition of any one of claim 1, 11, 12 or 21 effective to treat cancer.

32. The method of claim 31, wherein the cancer is selected from the group consisting of cancers of the blood, breast, lung, ovary, prostate, head, neck, brain, testes, kidney, pancreas, bone, spleen, liver and bladder; Kaposi's sarcoma; and leukemia.

33. The method of claim 32, wherein the cancer is leukemia.

34. The method of claim 33, wherein the leukemia is an acute leukemia.

35. The method of claim 34, wherein the acute leukemia is acute lymphocytic leukemia or acute myelocytic leukemia.

36. A vial containing the pharmaceutical composition of claim 1, 11, 12 or 21.

37. The pharmaceutical composition of claim 1, wherein the compound of formula 1 is purified.

38. The pharmaceutical composition of claim 11, wherein the compound of formula 2 is purified.

39. The pharmaceutical composition of claim 12, wherein the compound of formula 2 is purified.

40. The pharmaceutical composition of claim 21, wherein the compound of formula 3 is purified.

* * * * *